United States Patent
Topolovac et al.

(10) Patent No.: US 9,144,531 B2
(45) Date of Patent: Sep. 29, 2015

(54) VIBRATORY ACTUATOR AND DEVICE FOR SEXUAL STIMULATION

(75) Inventors: Michael Topolovac, San Francisco, CA (US); Edwin Wood, San Francisco, CA (US); Andrew Murphy, San Francisco, CA (US); Tian Yi Chang, San Francisco, CA (US); Kristrun Hjartar, Van Nuys, CA (US)

(73) Assignee: Crave Innovations, Inc., San Francisco, CA (US)

( * ) Notice: Subject to any disclaimer, the term of this patent is extended or adjusted under 35 U.S.C. 154(b) by 374 days.

(21) Appl. No.: 13/584,659

(22) Filed: Aug. 13, 2012

(65) Prior Publication Data

US 2014/0046127 A1    Feb. 13, 2014

(51) Int. Cl.
| | | |
|---|---|---|
| *A61H 19/00* | (2006.01) | |
| *A61H 23/00* | (2006.01) | |
| *A61H 23/02* | (2006.01) | |
| *A61H 23/04* | (2006.01) | |
| *A61N 1/36* | (2006.01) | |
| *A61H 9/00* | (2006.01) | |
| *A61N 5/06* | (2006.01) | |
| *A61N 1/05* | (2006.01) | |

(52) U.S. Cl.
CPC ............ *A61H 19/40* (2013.01); *A61H 19/34* (2013.01); *A61H 19/44* (2013.01); *A61H 23/00* (2013.01); *A61H 23/02* (2013.01); *A61H 23/0218* (2013.01); *A61H 23/04* (2013.01); *A61N 1/36007* (2013.01); *A61H 9/0078* (2013.01); *A61H 2023/0272* (2013.01); *A61H 2201/0107* (2013.01); *A61H 2201/0165* (2013.01); *A61H 2201/0207* (2013.01); *A61H 2201/0214* (2013.01); *A61H 2201/5002* (2013.01); *A61H 2201/5012* (2013.01); *A61H 2201/5015* (2013.01); *A61H 2201/5035* (2013.01); *A61H 2201/5038* (2013.01); *A61H 2201/5048* (2013.01); *A61H 2201/5097* (2013.01); *A61N 1/0524* (2013.01); *A61N 2005/0659* (2013.01)

(58) Field of Classification Search
CPC ................ A61H 19/44; A61H 19/34; A61H 2201/0153; A61H 23/0263; A61H 19/32; A61H 23/02; A61H 19/50; A61H 19/30; A61H 19/40; A61H 2201/1664; A61H 2201/1669; A61H 2201/5507; A61H 2201/5012
See application file for complete search history.

(56) References Cited

U.S. PATENT DOCUMENTS

| | | | |
|---|---|---|---|
| 8,821,421 B2 | 9/2014 | Imboden et al. | |
| 2004/0082831 A1* | 4/2004 | Kobashikawa et al. | 600/38 |
| 2010/0013610 A1* | 1/2010 | Schwieger | 340/407.1 |

* cited by examiner

*Primary Examiner* — Christine H Matthews
(74) *Attorney, Agent, or Firm* — Jeffrey Schox

(57) ABSTRACT

One variation of a device for sexual stimulation includes: an interaction module, a power module, and a control module. The interaction module includes a housing, a female power port supported by the housing, and a first and a second vibratory actuator coupled to the female power port, isolated from the housing, and supported by the housing. The power module includes a battery coupled to a male power port. The male power port is configurable between: a first configuration in which the male power port transiently couples to an external power source to charge the battery; and a second configuration in which the male power port transiently retains the interaction module and powers the vibratory actuators to generate haptic vibratory stimulation. The control module configured to control vibratory magnitude settings and vibratory pattern settings of the vibratory actuators based upon inputs at input regions.

15 Claims, 6 Drawing Sheets

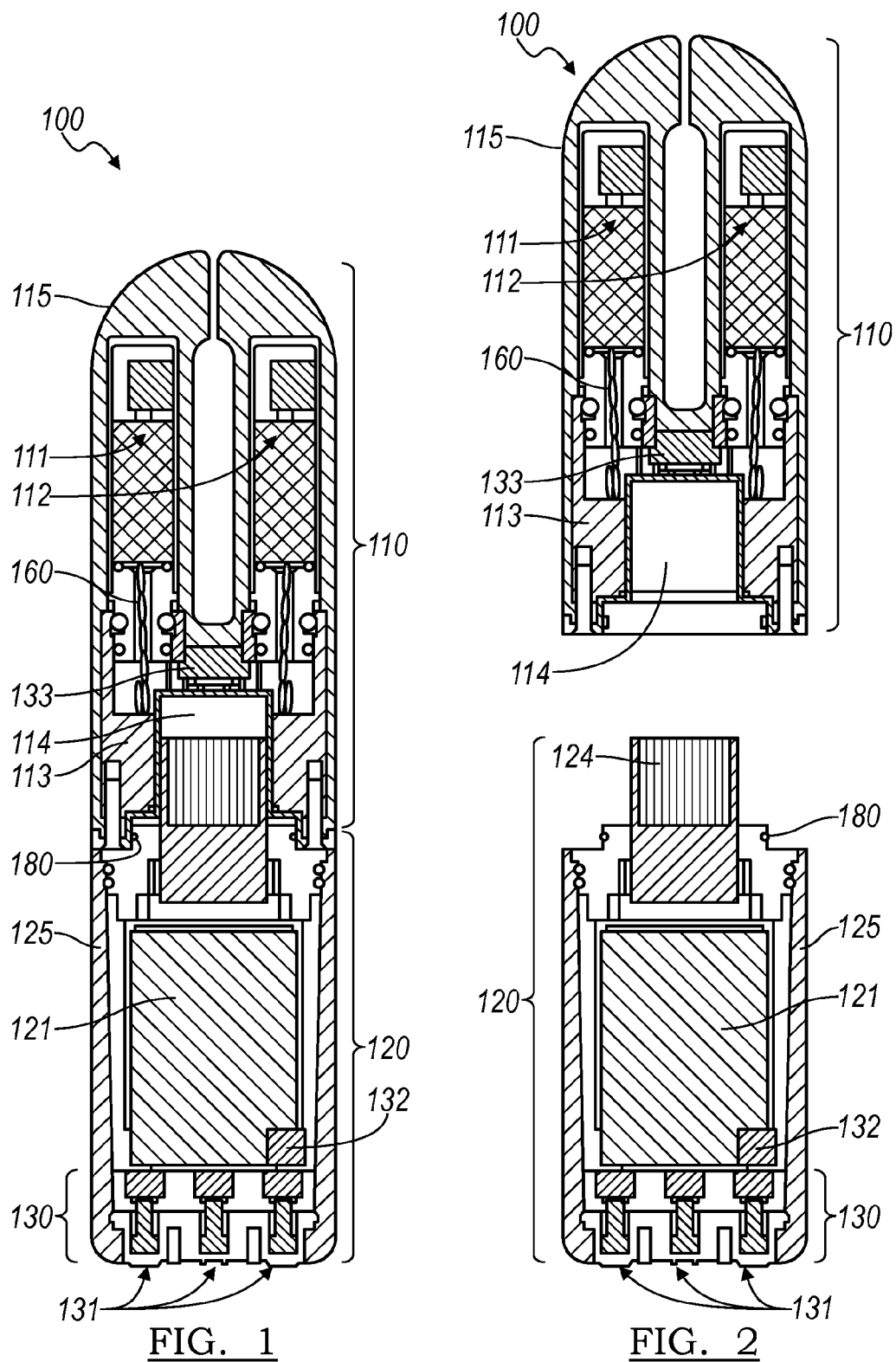

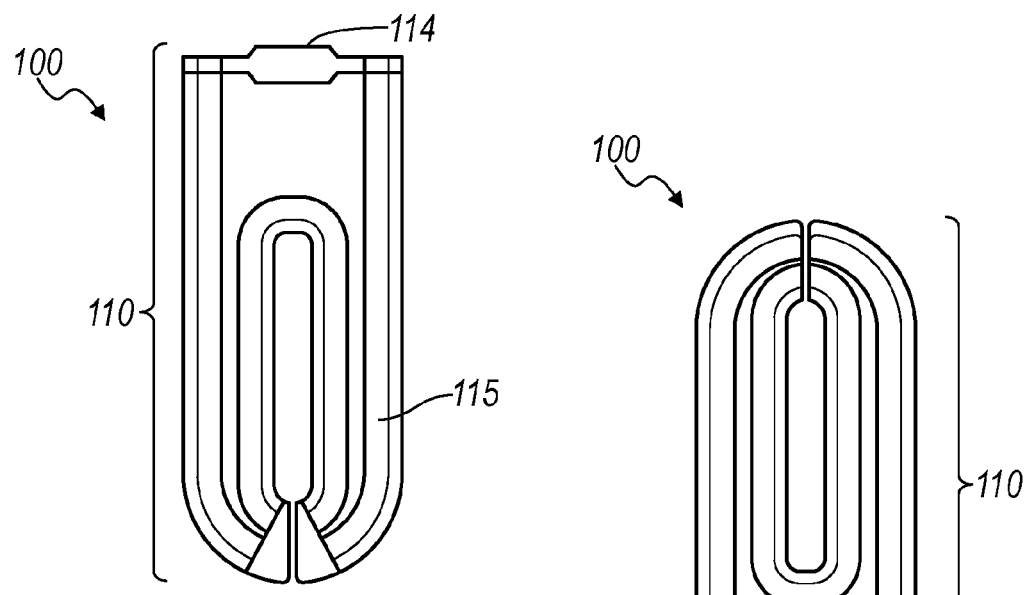
FIG. 3A
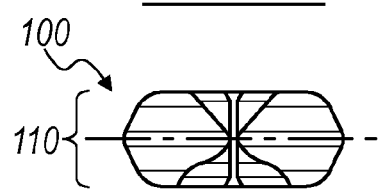
FIG. 3B
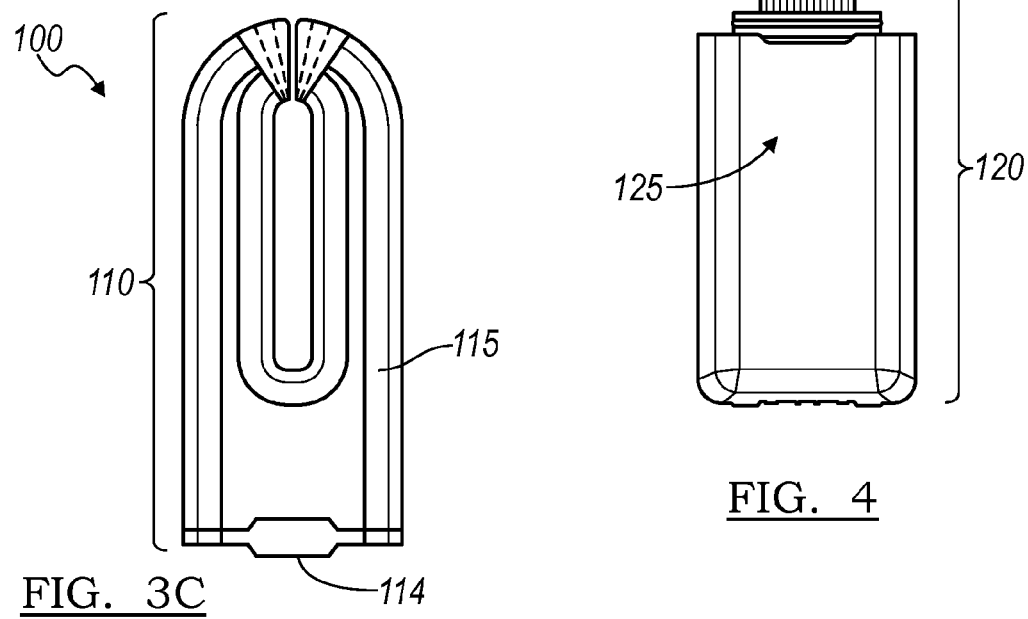
FIG. 3C
FIG. 4

US 9,144,531 B2

VIBRATORY ACTUATOR AND DEVICE FOR SEXUAL STIMULATION

TECHNICAL FIELD

This invention relates generally to the field of sexual paraphernalia, and more specifically to a new and useful vibratory actuator and a new and useful device for sexual stimulation in the field of sexual paraphernalia.

BACKGROUND

Vibrators and other sex toys are becoming increasing popular as sexual health is becoming increasingly recognized as essential to overall personal wellbeing, particularly for women. However, though typically recognized as very private and personal products, many sex toys retain functions that are excessively conspicuous, both when in use and when not. Therefore, there is a need in the field of sexual stimulation paraphernalia for a new and useful vibratory actuator and a new and useful device for sexual stimulation.

BRIEF DESCRIPTION OF THE FIGURES

FIG. 1 is a schematic representation of a preferred device in a first configuration;

FIG. 2 is a schematic representation of the preferred device in a second configuration;

FIGS. 3A, 3B, and 3C are elevation, plan, and elevation views, respectively, in accordance with one variation of an interaction module of the preferred device;

FIG. 4 is a schematic representation of one variation of the preferred device;

DESCRIPTION OF THE PREFERRED EMBODIMENTS

Figures 5, 6:
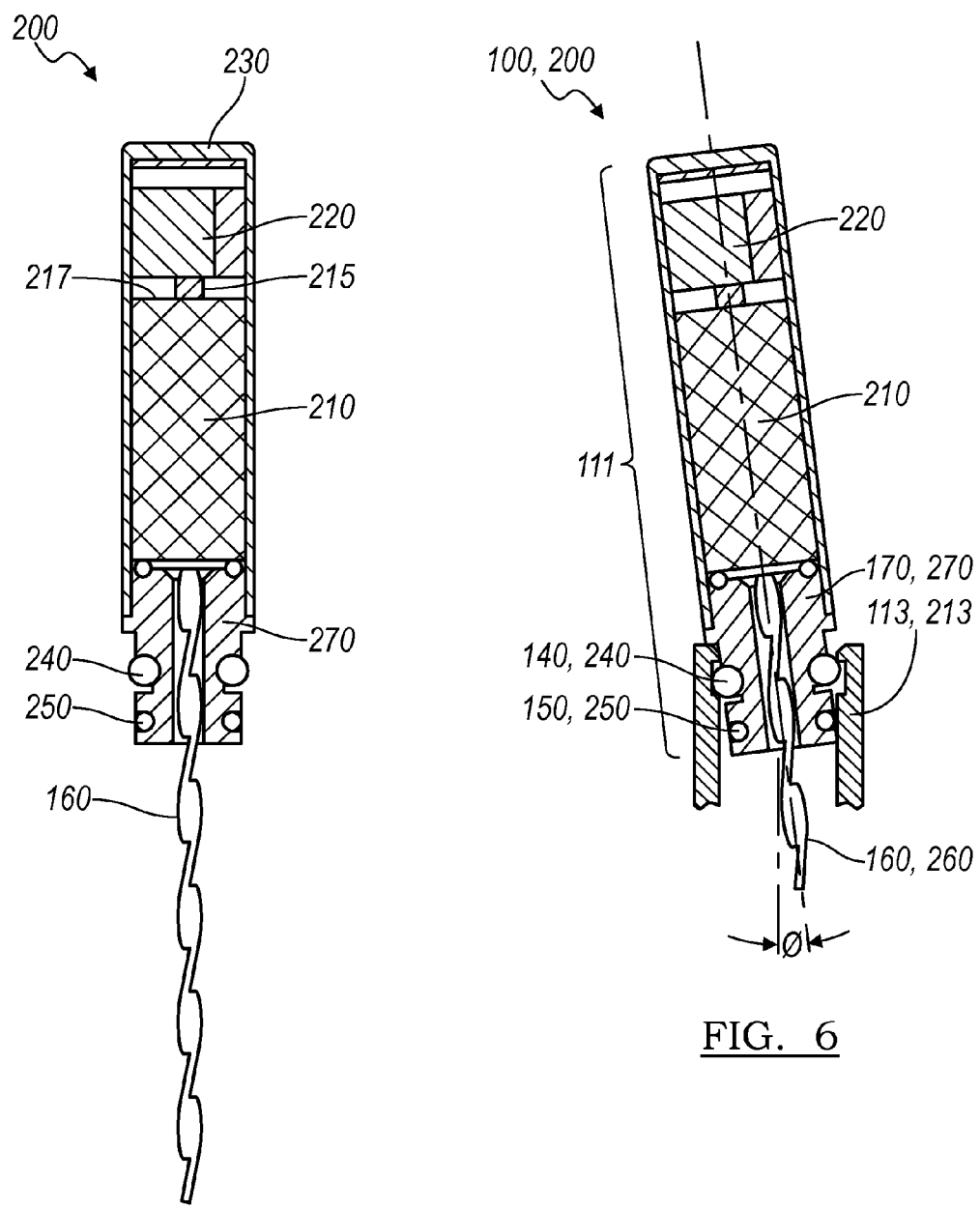
FIG. 5 is a schematic representation of a preferred vibratory actuator.
FIG. 6 is a schematic representation of one variation of the preferred device and the preferred vibratory actuator.

The following description of the preferred embodiment of the invention is not intended to limit the invention to these preferred embodiments, but rather to enable any person skilled in the art to make and use this invention.

1. Device for Sexual Stimulation

As shown in FIGS. 1 and 2, a device 100 for sexual stimulation includes: an interaction module 110, a power module 120, and a control module 130. The interaction module 110 includes a housing 113, a female power port 114 supported by the housing 113, and a first vibratory actuator 111 and a second vibratory actuator 112 coupled to the female power port 114, isolated from the housing 113, and supported by the housing 113. The power module 120 includes a rechargeable battery 121 and a male power port 124 coupled to the battery 121. The male power port 124 is configurable between: a first configuration in which the male power port 124 transiently couples to a female charge port of an external power source to charge the battery 121 (shown in FIG. 9); and a second configuration in which the male power port 124 transiently retains the power module 120 against the interaction module 110 via the female power port 114 of the interaction module 110 and communicates power to the vibratory actuators 111, 112, via the female power port 114, to generate haptic vibratory stimulation. The control module 130 includes a plurality of input regions 131 and is configured to control vibratory magnitude settings and vibratory pattern settings of the vibratory actuators 111, 112 based upon inputs on the input regions 131.

In a variation of the device 100 for sexual stimulation, the interaction module 110 includes a housing 113 a female power port 114 supported by the housing 113, and a haptic stimulation unit coupled to the female power port 114 and configured to stimulate soft tissue of a user. In this variation, the male power port 124 is operable between: a first configuration in which the male power port 124 transiently couples to a female charge port of an external power source to charge the battery 121; and a second configuration in which the male power port 124 transiently retains the power module 120 against the interaction module 110 via the female power port 114 of the interaction module 110 and communicates power to the haptic stimulation unit, via the female power port 114, to stimulate the sex organ. Furthermore, the control module 130 includes a plurality of input regions and is configured to control stimulation settings of the haptic stimulation unit based upon inputs on the input regions 131. This variation of the device 100 therefore implements a haptic stimulation unit, which can include any one or more of a vibratory actuator, a heating element, a cooling element, a linear or non-linear actuator, or any other suitable stimulatory unit, element, or component.

Figure 7:
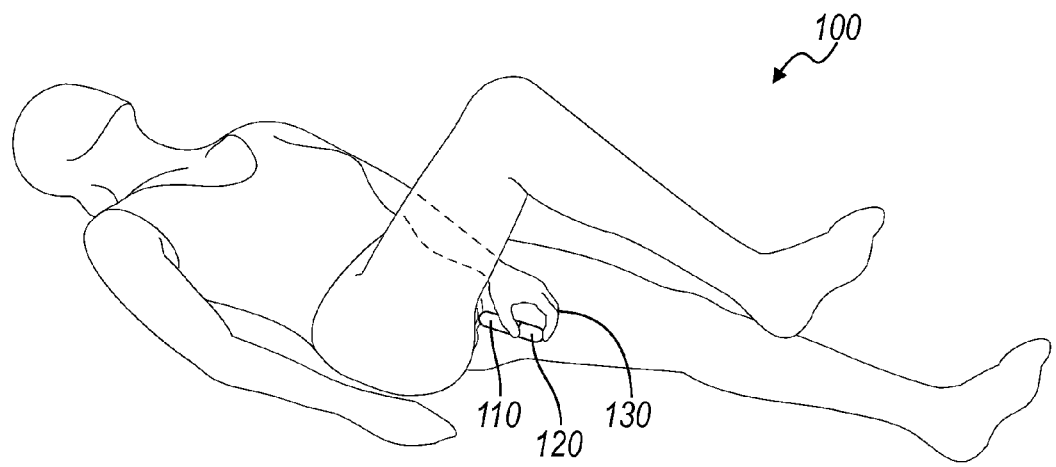
FIG. 7 is a schematic representation of a use scenario in accordance with the preferred device in the second configuration.

The device 100 preferably functions as a sex toy and can be manipulated by a user to stimulate a sex organ of the user or a sex organ of a partner of the user. The device 100 may be used with the intent of initiating or aiding in orgasm. The device 100 includes an interaction module, configured to contact and stimulate a sex organ of a user, and a power module, configured to power the interaction module 110 and to be held by the user when engaging the interaction module 110 against or inside a sex organ, as shown in FIG. 7. When the interaction module 110 and the power module 120 are assembled in the second configuration, shown in FIG. 2, the interaction module 110 sources power from the power module 120 to generate a haptic stimulation suitable for sexual stimulation. The device 100 further enables the user to separate the power module 120 from the interaction module 110 such that visual or tactile exposure to the interaction module 110, such as by the user and other observers, can be substantially limited while the device 100 is not in use and while the battery 121 is recharged. Generally, the power module 120 and the interaction module 110 are preferably separable such that the portion of the device 100 that contacts or is inserted into a sex organ (i.e. the interaction module 110) can be set aside or stored while a discreet portion of the device 100 (i.e. the power module 120) is recharged in plain view and through a common power source. For example, the male power port 124 of the power module 120 can plug into a Universal Serial Bus (USB) port on a computer (shown in FIG. 9), a standard wall outlet, or a coaxial charging jack to charge the battery 121 while the interaction module 110 is stored in a bedside table. Therefore, the particular configuration of the device 100 can minimize handling or visual exposure of the interaction module 110, which can be substantially more personal and more conspicuous than the power module 120, when the device 100 is not in use. This particular configuration can further permit the less conspicuous, more innocuous (e.g., less personal) power module to be charged without attracting scrutiny from observers.

The interaction module 110 of the device 100 includes a housing 113, a female power port 114 supported by the housing 113, and a first and a second vibratory actuator 111, 112 coupled to the female power port 114, isolated from the housing 113, and supported by the housing 113. The interaction module 110 is preferably configured to stimulate an external female sex organ, such at the clitoris, labia, vulva, perineum, anus, nipple, breast, or areola. The interaction module 110 can additionally or alternatively be configured to stimulate a male sex organ, such as the penis, scrotum, or anus. The interaction module 110 can additionally or alternatively function to stimulate an internal sex organ, such as the vagina, G-spot, prostate, rectum, or any other internal or external portion of the body of a female or male user. The interaction module 110 preferably generates vibratory stimulation through an electromechanical actuator, such as an electric motor coupled to a counterweight, a piezoelectric transducer coupled to a mass, a charged diaphragm coupled to a mass, or any other linear or rotary actuator manipulating an (eccentric) mass to generate a vibration. Furthermore, the counterweight or mass can include a bladder system with a hydraulic or pneumatic cavity configured to fill and drain to adjust the vibratory output or "feel" of the vibratory actuator.

Figure 11A:
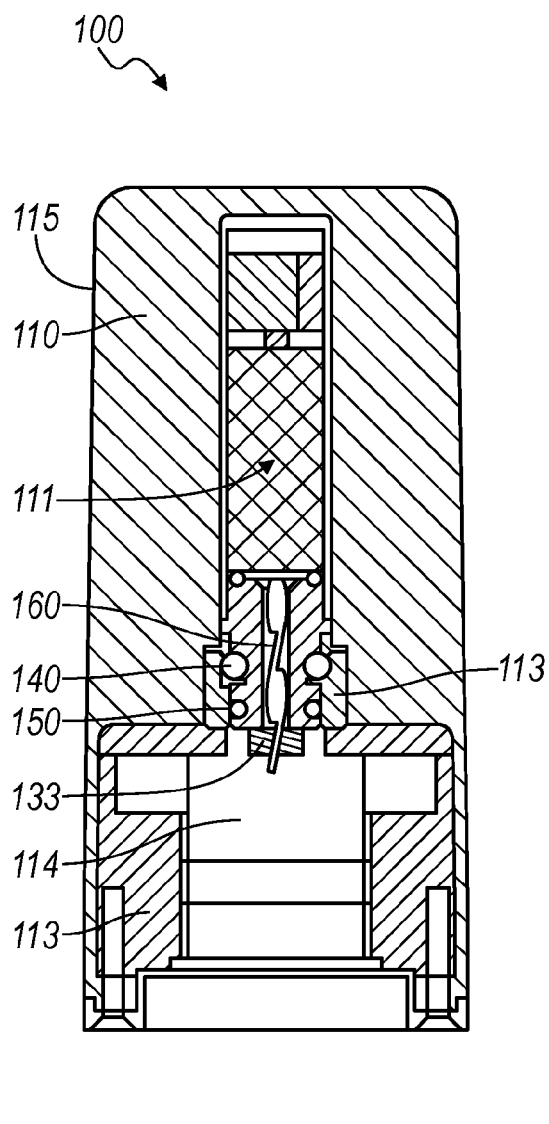
FIGS. 11A and 11B are schematic representations in accordance with one variation of an interaction module of the preferred device.
Figure 11B:
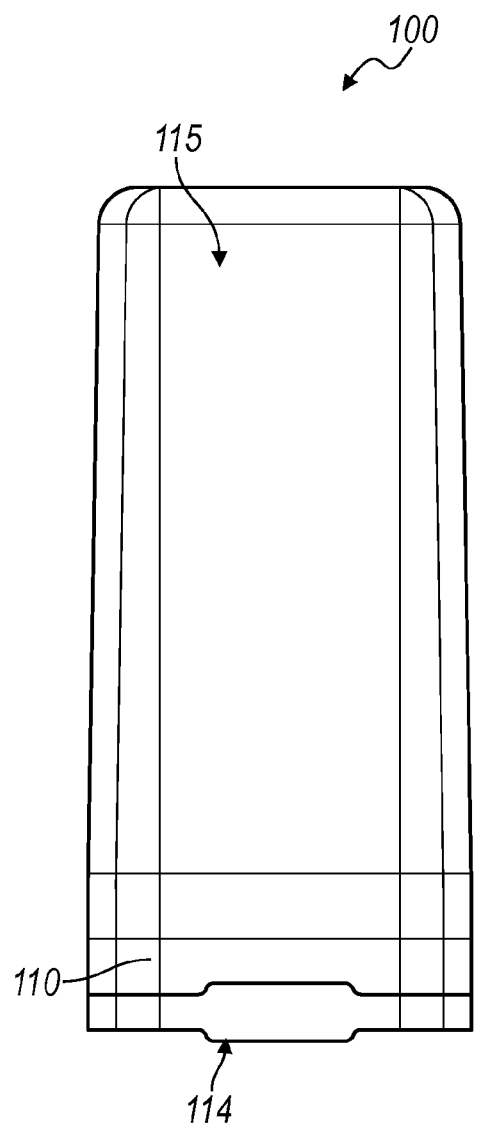

However, as described in the variation of the device 100 above, the interaction module 110 can include any other element or component to stimulate a sex organ or soft tissue of the user in any other way. For example, the interaction module no can include a heating or cooling element to heat or cool a portion of the body of the user, a set of electrodes to output electrical shocks or pulses to a portion of the body of the user, lights or a display to output visual cues, or a smell module to provide olfactory sensations. The interaction module 110 can also haptically stimulate the user with non-vibratory mechanical motion, such as by bending, twisting, curling, flexing, elongating, or inflating. Alternatively and as shown in FIGS. 11A and 11B, the interaction module 110 can include a single vibratory actuary 111. The interaction module 110 can therefore include any other suitable electrical, electromechanical, or electrochemical component and/or linkage to stimulate a sex organ or soft tissue of a user.

As shown in FIGS. 1 and 2, one example implementation of the device 100 includes a vibratory actuator 111 that is an electromechanical motor with an output shaft that supports a counterweight (i.e. eccentric mass). The motor is preferably a DC micromotor, though the motor can alternatively be a brushless motor, servomotor, stepper motor, or any other suitable type of motor of any other size. As shown in FIGS. 1 and 5, the vibratory actuator 111 can further include an enclosure that shields the output shaft and counterweight when in motion. The motor is preferably substantially circular in cross-section, and the enclosure is preferably cylindrical with a shoulder proximal a closed end such that the motor can be slip-fit into the enclosure, output shaft first, with the shoulder retaining the face of the motor proximal the output. A plug 170 can then be pressed into the open end of the enclosure to capture the motor. As shown in FIGS. 1 and 5, the assembly can further include an o-ring or other isolator between the plug 170 and the back face of the motor to absorb manufacturing tolerances of the assembly, such as length or diameter tolerances of the enclosure, the plug 170, or the motor. As shown in FIG. 1, motor leads 160 preferably pass through a bore in the plug 170, and the plug 170 preferably further includes a first external circular groove adjacent a second external circular groove, the first and second grooves configured to capture a first isolator 140 and a second isolator 150, respectively. The first isolator 140 preferably pivotably couples the motor to the housing 113, and the second isolator 150 preferably contacts a surface of the housing 113 to define a soft pivot endstop. Generally, the first isolator 140 preferably substantially constrains the vibratory actuator in three degrees of translation and enables the vibratory actuator in at least two degrees of rotation up to the compressible endstop defined by the second isolator 150. The first and second isolators 140, 150 are preferably o-rings that engage the circular grooves in the plug 170, wherein the second isolator 150 is of an outer diameter less than the outer diameter of the first isolator 140, and wherein the second isolator 150 is of a cross-sectional area less than the cross-sectional area of the first isolator 140. In this example implementation and as shown in FIG. 6, the housing 113 preferably includes a receptacle (e.g., an internal bore with internal shoulder) that captures the plug 170 and isolators 140, 150 and enables the vibratory actuator 111 to pivot about the first isolator 140, wherein the second isolator 150 limits maximum off-axis deflection of the motor assembly (e.g., less than 10° off axis). This soft coupling between the housing 113 and the vibratory actuator 111 preferably isolates counterweight-induced vibrations from the housing 113, which can limit vibrations communicated to the power module 120 via the housing 113, the female power port 114, and the male power port 124 when the device 100 is in use. Therefore, the soft coupling between the housing 113 and the vibratory actuator 111 can render the device 100 more comfortable for the user by reducing vibrations transmitted from the vibratory actuator 111 into a hand supporting the power module 120 while in use.

However, features or elements of the foregoing example implementation of the vibratory actuator 111 can be incorporated into any other one or more components. For example, the enclosure can incorporate the external circular grooves, thereby eliminating the need for the plug 170. In another example, the enclosure can define internal circular grooves that capture internal isolators (e.g., o-rings), wherein the isolators both retain the motor within the enclosure and pivotably couple the enclosure to a protrusion extending from the housing 113. In yet another example, the enclosure can encompass the counterweight and only a portion of the length of the motor, and the isolators can engage external circular grooves machined or formed into the motor casing. In other example implementations, the vibratory actuator 111 can couple to the housing 113 via a ball-in-socket joint, a single rubber sleeve or gasket arranged between the housing 113 and the enclosure, a flex- or fluid-coupling, a four-bar linkage in which the housing 113 and enclosure each define a linkage, or any other suitable mechanical linkage or coupling that mechanically couples the motor and/or the enclosure to the housing 113 with adequate vibration isolation. Furthermore, the motor, counterweight, output shaft, enclosure, isolators, or housing receptacle or protrusion that engages the isolators can be of any other form, dimension, geometry, or arrangement.

Housing material selection can affect transmission of vibrations from the vibratory actuators 111, 112 directly into the body of the user and/or into the power module 120. Generally, the housing 113 is preferably a substantially rigid material, such as plastic or metal, to minimize low-frequency vibration transmission into the power module 120, and the housing 113 can be machined from billet, die cast, investment cast, stamped, etched, injection molded, stamped, formed, or manufactured according to any one or more techniques or methods. For example, the housing 113 can be diecast zinc, machined aluminum, injection molded high-density polyethylene (HDPE) or nylon, or stamped from stainless steel sheet. Alternatively, the housing 113 can be of a material that is substantially elastic or flexible, such as with a resonant frequency outside of an operating frequency range of the vibratory actuators 111, 112. For example, the housing 113 can be molded rubber. However, the housing 113 can be any other suitable material and can be manufactured via any other method or combination of methods.

The interaction module 110 preferably includes a pair of electromechanical vibratory actuators, each powered through a pair of leads electrically coupled to a printed circuit board (PCB) coupled to the female power port 114. The PCB can also support the female power port 114 against the housing 113. The female power port 114 is preferably a standard female USB socket including four pins. However, the female power port 114 can include a mini- or micro-USB port, a coaxial power jack, a Thunderbolt jack, an audio-type jack, Firewire, eSATA, HDMI, or any other suitable type or form of jack or digital port. In one variation of the device 100, the interaction module 110 includes a male or sexless jack or port rather than a female port, and the power module 120 includes a corresponding female or sexless jack or port. The PCB preferably defines an electrical interface between the female power port 114 and the vibratory actuator 111 leads, though the female power port 114 can directly or indirectly interface with the motor leads through any other component.

In one example implementation in which the female power port 114 is a female USB socket, the PCB includes traces that communicate independent power signals from the female power port 114 to the vibratory actuators 111, 112. In this example implementation, a dedicated ground pin of the female power port 114 is preferably connected to one lead from each of the vibratory actuators 111, 112. A first standard digital pin of the female power port 114 is connected to a second lead of one vibratory actuator, and a second standard digital pin of the female power port 114 is connected to another lead of the second vibratory actuator 112 such that independent power signals can be independently communicated through the female power port 114 and over a common ground loop to independently control the vibratory actuators 111, 112. However, one or more independent power signals can be communicated to the vibratory actuators 111, 112 via the female power port 114 and/or PCB to control the vibratory actuators 111, 112 in any other way.

Figure 10:
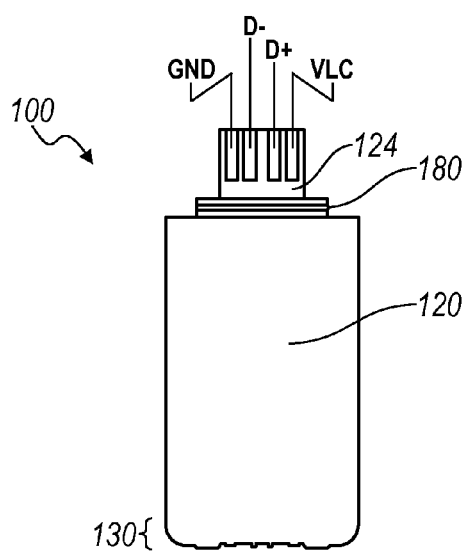
FIG. 10 is a schematic representation in accordance with one variation of a power module of the preferred device.

In another example implementation in which the female power port 114 is a female USB socket, the PCB includes a driver 133 (e.g., a motor driver) for each vibratory actuator 111, 112, wherein each driver 133 receives an independent digital control signal via a digital pin of the female power port 114 and distributes a power signal, in accordance with the digital control signal, from a power pin of the female power port 114 to a corresponding vibratory actuator. (In this and other example implementations, the driver(s) 133 are preferably a portion of the control module 130.) In this example implementation, the USB port includes a first pin that is an analog power pin, a second pin that is a ground pin, a third pin that is a first digital pin, and a fourth pin that is a second digital pin, as shown in FIG. 10. In this configuration, the drivers 133 and vibratory actuators 111, 112 are preferably connected to the ground pin to define a common ground path, and the drivers 133 preferably siphon current from the power pin to enable driver operation. This configuration can reduce noise or inductive interference across analog and/or digital circuitry within the interaction module, no, power module 120, and/or control module 130, thus enabling uninterrupted operation of a processor 132, controller, or memory arranged within any of the modules 110, 120, 130.

As shown in FIG. 4, the interaction module 110 preferably further includes a polymer sleeve that sheaths a portion of the housing 113 and the vibratory actuators 111, 112. The polymer sleeve 115 is preferably a silicone polymer that is molded around the housing 113 and the vibratory actuators 111, 112 (or haptic stimulation units) in situ to define a waterproof, dustproof, and hermetic sheath over the portion of the interaction module 110. Alternatively, the polymer sleeve 115 can be molded separately and subsequently stretched or installed over the housing 113 and vibratory actuators 111, 112 to define the waterproof, dustproof, and hermetic barrier around the interaction module 110. The polymer sleeve 115 preferably terminates proximal the female power port 114, and at least one of the interaction and power modules 110, 120 preferably includes a seal 180 proximal a respective power port such that the seal 180 and polymer sleeve can cooperate to define a complete waterproof, dustproof, and hermetic barrier around the interaction module 110 when the interaction and power modules are assembled. For example, the seal 180 can be an o-ring seal around the male power port 124, as shown in FIG. 2, wherein the seal 180 engages the female power port 114 to cooperate with the polymer sleeve 115 to define a barrier with an Ingress Protection Rating of 25 or higher. Alternatively, the interaction module 110 can include a metal parting band that supports the female power port 114 and engages a seal around the male power port to seal the device 100 in the second configuration, as show in FIG. 1. The polymer sleeve 115 preferably also defines a substantially smooth surface that is food-safe, body-safe, hygienic, and cleanable with minimal internal or concave surfaces that can trap or hold dirt, bacteria, or fluid.

In one example implementation of the device 100 shown in FIGS. 1 and 2, the housing 113 supports the vibratory actuators 111, 112 with axes substantially parallel and offset when not in use. When in operation or held against a sex organ (as show in FIG. 7), the vibratory actuators 111, 112 can deflect off axis, such as by pivoting about the housing-actuator junction by up to several degrees. In this example implementation, the polymer sleeve 115 preferably deflects with the vibratory actuators 111, 112 but does not substantially retard transmission of vibrations from the vibratory actuators 111, 112 into the body of the user. Furthermore, the vibratory actuators 111, 112 are preferably powered by independent power signals and can therefore generate vibrations independently. Each vibratory actuator is therefore preferably mechanically decoupled from the other vibratory actuator via the isolators 140, 150 to define a distinct vibration source, and the polymer sleeve 115 preferably sheaths but does not connect the free ends of the vibratory actuators 111, 112, as shown in FIGS. 1 and 2. This geometry can enable the device 100 to output distinct, tactilely-discernible vibration patterns from multiple haptic stimulation sources. In one example, the device 100 can repetitively pulse one vibratory actuator and then the other vibratory actuator. In another example, the device 100 can repetitively ramp the vibratory motors up and down and out of phase, such as 45°, 90°, or 180° out of phase. In yet another example, the device 100 can continuously drive one vibratory motor and pulse the other vibratory motor at pseudorandomly-selected times and power settings, such as every one to five seconds for between one half and two seconds between 50% and 100% power.

The polymer sleeve 115 can further define interaction surfaces proximal the vibratory actuators 111, 112. In one example implementation shown in FIG. 8, the polymer sleeve 115 includes ripples, studs, cilia-like structures, or other tactilely-distinct features adjacent each vibratory actuator. These features can be pattered uniformly around each vibratory actuator or can be arranged on specific areas of the polymer sleeve 115. For example, the polymer sleeve 115 can define ripples on one side of the vibratory actuators 111, 112 and cilia-like structures on the opposite side of the vibratory actuators 111, 112 such that the user can flip the device 100 for application of different sensory stimulation. In another example implementation shown in FIGS. 1 and 2, the polymer sleeve 115 defines a split loop over the housing 113 and vibratory actuators, wherein the polymer material extends from each vibratory actuator to the opposite vibrator actuator to define a pair of cusps. In this example implementation, the geometry of the polymer sleeve 115 is preferably configured to accommodate the clitoris of a female user, either within the split loop or between the cusps. In this variation and as shown in shown in FIGS. 3A, 3B, and 3C, the polymer sleeve 115 can further include a chamfer of a first size on one side of the cusps and a surface of a different profile on the opposite side of the cusps such that a user can select a surface geometry that best accommodates the unique size, shape, or location of the user's clitoris. However, the polymer sleeve 115 can be of any other geometry, include any other stimulation feature, and define any other stimulation surface configured to accommodate or stimulate any other sex organ or portion of the body of the user.

Figure 8:
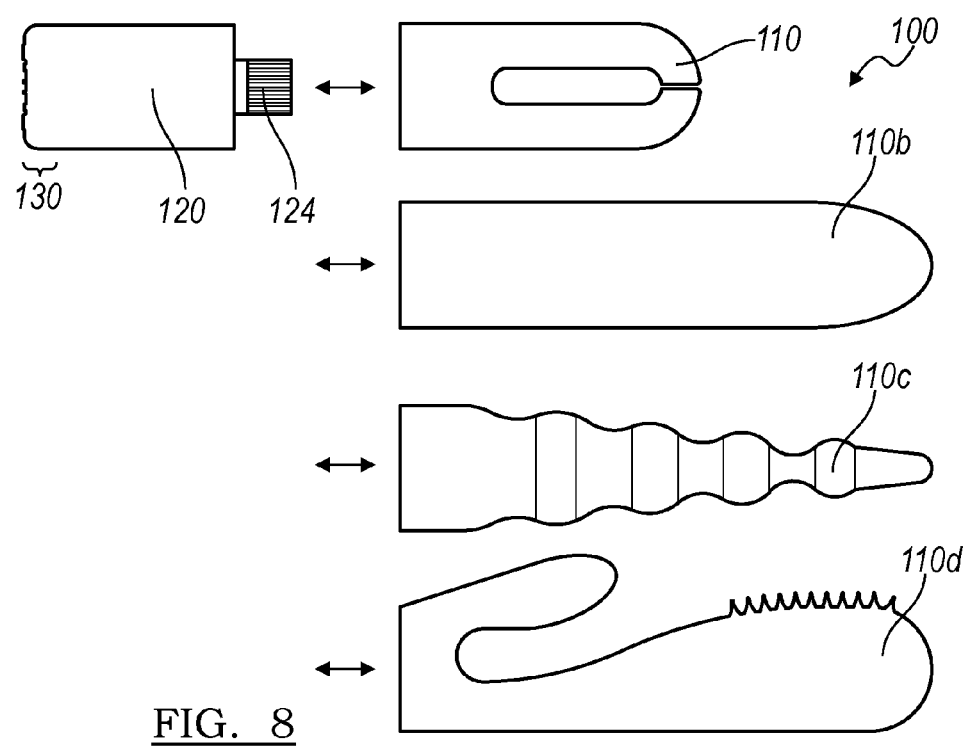
FIG. 8 is a schematic representation of one variation of the preferred device.

The interaction module 110 preferably includes a pair of vibratory actuators 111, 112, though the interaction module 110 can include any other number of vibratory actuators or haptic stimulation units of any other type or form, supported by the housing 113 in any other way, and powered in any other way to output any other suitable haptic stimulation. In example implementations, the interaction module 110 can include: one vibratory actuator; three (or more) vibratory actuators controlled by a processor via a multiplexer or serial-in, parallel-out (SIPO) shift register electrically coupled to three (or more) motor drivers; a vibratory actuator and a heating element; or two vibratory actuators and an infrared emitter. However, the interaction module 110 can include any other suitable haptic stimulation unit, component, or element. Furthermore, the interaction module 110 can define a geometry or include a haptic stimulation unit suitable for stimulation of a particular sex organ. In example implementations shown in FIG. 8, the interaction module 110 can include: a vibratory actuator adjacent a blunt (e.g., convex, narrowly protruding) surface suitable for clitoral stimulation (interaction module 110); a vibratory actuator within an elongated (e.g., phallic) member suitable for inter-vaginal stimulation (interaction module 110b); or a vibratory actuator within a deeply-ribbed elongated member suitable for inter-rectal stimulation (interaction module 110c). In another implementation, the interaction module 110 and power module 120 can each define semicircular swept sections that assemble in the second configuration to define a ring, wherein the interaction module 110 includes a vibratory actuator such that the device 100 is suitable for penile stimulation. The interaction module 110 can further define a geometry suitable for stimulation of multiple sex organs simultaneously. For example and as shown in FIG. 8, an interaction module nod can include a vibratory actuator within an elongated member suitable for inter-vaginal stimulation and a second vibratory actuator within a short curved member proximal one end of the elongated member and suitable for simultaneous clitoral stimulation. However, the interaction module 110 can include any other haptic stimulation unit in any other quantity or combination, and the interaction module 110 can be of any other form or geometry suitable for stimulation of any other one or more portions of the body of the user.

Figure 9:
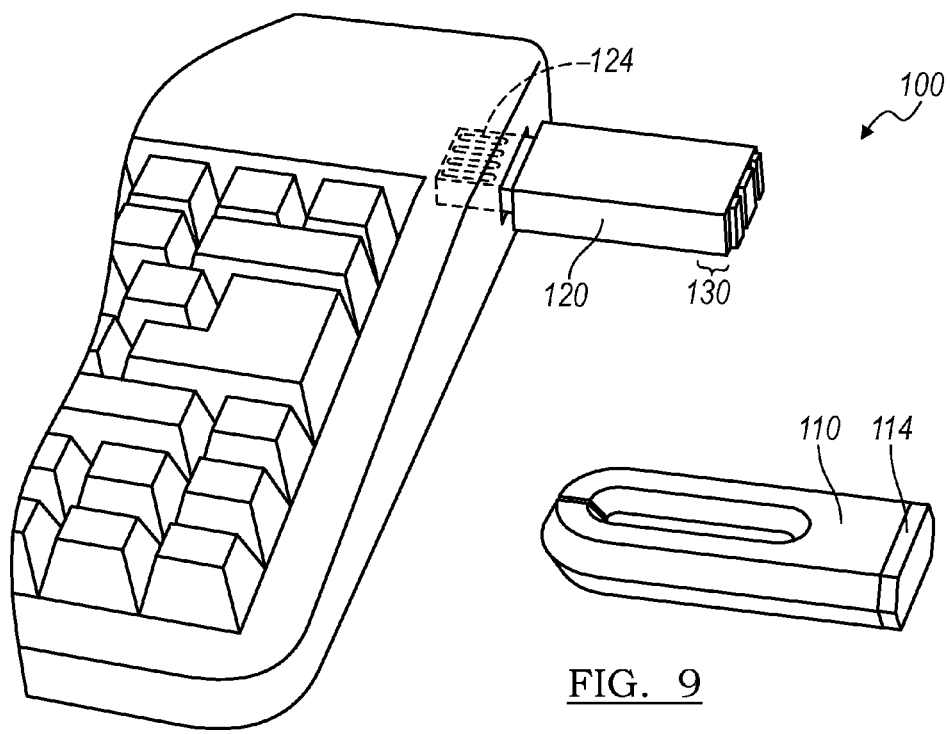
FIG. 9 is a schematic representation of a use scenario in accordance with the preferred device in the first configuration.

The power module 120 of the device 100 includes the rechargeable battery 121 and the male power port 124 coupled to the battery 121, wherein the male power port 124 is configurable between the first configuration and the second configuration. As shown in FIGS. 2 and 9, in the first configuration, the male power port 124 transiently couples to a female charge port of an external power source to charge the battery 121. As shown in FIG. 1, in the second configuration, the male power port 124 transiently retains the interaction module 110 via the female power port 114 and communicates power to the vibratory actuators 111, 112, via the female power port 114, to generate haptic vibratory stimulation. As described above, the power module 120 is preferably separable from the interaction module 110 such that the device 100 can be recharged while the interaction module 110, which can be substantially more personal and less discreet than the power module 120, is set aside. The battery 121 can be any of a lithium-polymer, lithium-ion, lithium iron phosphate, nickel metal hydride, or any other suitable type of rechargeable electric battery. The battery 121 preferably does not require removal from the power module 120 to be recharged and is instead preferably recharged by plugging the power module 120 into an external electric power source, such as a computer (e.g., via a USB port, shown in FIG. 9) or a wall outlet.

However, the battery 121 can store any other type of energy in any other form. For example, the battery 121 can store chemical energy in the form of hydrogen, wherein the male power port 124 sources hydrogen from an external source, the battery 121 stores the hydrogen, and an onboard generator or fuel cell converts the hydrogen into electrical energy to power the vibratory actuators 111, 112 or haptic stimulation units. Alternatively, the battery 121 can store hydraulic pressure, wherein the male power port 124 communicates hydraulic pressure, via the female power port 114, to the vibratory actuators to induce a vibration. The battery 121 (i.e. power storage module) can also store pneumatic pressure, vacuum, heat, steam, or any other electrical, chemical, or mechanical form of energy to subsequently power the interaction module 110.

The power module 120 preferably further includes a charging circuit that controls current and/or voltage signals across the battery leads as the battery 121 is charged. In an example implementation in which the battery 121 is a lithium-ion battery and the male power port 124 is configured to engage a USB port on a computer, the charging circuit can first deliver a near-constant amperage at increasing voltage to the battery 121 until a desired battery voltage is reached, followed by diminishing current at near-constant voltage until the battery 121 reaches full charge saturation. If the power module 120 remains connected to the computer or other power source, the charging circuit can further supply topping charge if the battery 121 discharges over time (e.g., due to leakage currents in integrated circuits within the device 100). Furthermore, the charging circuit can communicate with a USB port on a computer, via data (i.e. digital) pins on the male power port 124, to source additional current from the port. For example, without active communication between the charge circuitry and the computer USB port, the power module 120 may only source 150 mA from the computer USB port. However, by actively communicating with the computer USB port through the USB data pins, the charging circuit can request a 500 mA source current from the computer USB port, which can enable faster battery charging.

The power module 120 preferably further includes a power-conditioning circuit. The power-conditioning circuit can include a voltage regulator, a buck circuit, a boost circuit, or other suitable electric circuit that transforms the output of the battery 121 into signal of desired voltage or current. For example, the battery 121 can output a nominal 3.7V, and the power-conditioning circuit can boost the battery output voltage to 5.0V nominal to power a processor that controls the vibratory actuators 111, 112. Furthermore, the power-conditioning circuit can regulate the output of the battery 121 from 3.7V nominal to a maximum of 2.0V to prevent damage to a motor or other component within a vibratory actuator 111 or haptic stimulation unit. However, the power-conditioning circuit can function in any other way to condition signals from the battery 121 to power various components and systems within the device 100. Furthermore, the power-conditioning circuit and/or the charging circuit can be arranged within the interaction module 110 rather than within the power module 120.

As described above, the male power port 124 is configurable between a first configuration and a second configuration, wherein the male power port 124 communicates a power signal into the power module 120 (e.g., into the battery 121) from an external source in the first configuration, and wherein the male power port 124 communicates a power signal from the battery 121 and into the interaction module 110 in the second configuration. The male power port 124 preferably includes a set of pins, tabs, conductive surfaces, etc. configured to engage a standard charging jack to charge the battery 121 in the first configuration. The male power port 124 is further configured to communicate power and/or control signals to the interaction module 110 over at least some of the same pins, tabs, surfaces, etc. to power and/or control the vibratory actuators 111, 112 or haptic stimulation unit(s) in the second configuration. The male power port 124 is preferably a standard male USB plug, though the male power port 124 can be a mini- or micro-USB port, a coaxial power jack, a Thunderbolt jack, an audio-type jack, or any other suitable male or female plug, receptacle, or socket.

In the example implementation in which the male power port 124 is a male USB plug, the male power port 124 preferably transmits an analog current signal from a female USB socket of an external power source (e.g., a computer, a wall adapter) via a dedicated standard ground pin and a dedicated standard power pin (e.g., VCC pin). As described above, the male power port 124 can further communicate with the external power source, via a digital send and digital receive pin (i.e. digital I/O pins), to source additional current from the external power source. In one example implementation described above in which one driver 133 per vibratory actuator is arranged within the power module 120, the power module 120 (or control module 130) preferably decouples digital circuitry from the digital I/O pins and instead couples the drivers 133 to the digital I/O pins. This configuration can enable communication of analog motor signals to the interaction module 110 to activate the vibratory actuators 111, 112 via the female power port 114, over a common ground loop including the dedicated ground pin. In this example implementation, digital I/O pins of the male power port 124 can therefore send and receive digital signals and transmit analog signals.

In another example implementation described above in which the drivers 133 are arranged within the interaction module 110, the male power port 124 preferably couples power and ground terminals of the battery 121 or power-conditioning circuit to the interaction module 110 via the dedicated power and ground pins. The male power port 124 preferably further communicates digital motor control signals from the processor 132 to the drivers 133 via the digital I/O pins to activate the vibratory actuators 111, 112. In this example implementation the vibratory actuators 111, 112 are preferably powered by the drivers 133 via a common power and ground loop. However, the male power port 124 can communicate digital and/or analog signals with the external power source and/or with the interaction module 110 in any other way.

As shown in FIG. 4, the power module 120 preferably further includes a second housing 125 that defines a waterproof, dustproof, and hermetic boundary around the battery 121 in the second configuration (i.e. when the interaction module 110 and power module are assembled). Generally, the second housing 125 preferably cooperates with the seal 180 and the polymer sleeve 115 to enclose and seal the power ports 114, 124, the vibratory actuators 111, 112 or haptic stimulation units, the battery 121, and the control module 130 against fluid, dust, or other ingress in the second configuration. The second housing 125 and the polymer sleeve 115 can further enclose and seal a charge circuit, a power-conditioning circuit, a processor 132, a driver 133, a memory module, and/or any component within the device 100. The second housing 125 is preferably a substantially rigid material, such as a metal or rigid plastic, though the housing 113 can alternatively include a rigid substrate with a soft sheath or coating, such as a polymer sleeve similar to the polymer sleeve 115 of the interaction device. However, the exterior surface of the second housing 125 is preferably food-safe, body-safe, hygienic, and cleanable with minimal internal or concave surfaces that can trap or hold dirt, bacteria, or fluid. Furthermore, the outer cross-section of the second housing 125 proximal the male power port 124 is preferably substantially similar to the outer cross-section of the interaction module 110 proximal the female power port 114 such that the device 100 appears substantially continuous across the power and interaction modules in the second configuration (i.e. when assembled), as shown in FIG. 1.

In a variation of the second configuration, the interaction and power modules 110, 120 are separated by an extension cable coupled at a first end to the female power port 114 and on a second opposite end to the male power port 124. In this variation of the second configuration, the power module 120 can power and/or control the interaction module 110 substantially remotely via the extension cable, which can enable the use to stimulate a different sex organ, stimulate a sex organ in a different way, and/or stimulate a sex organ more comfortable. The extension cable preferably includes a seal at both the first end and the second end, wherein the seals cooperate with the interaction module 110 and the power module 120 to define waterproof, dustproof, and hermetic barriers around the modules 110, 120 in this variation of the second configuration.

The control module 130 includes a plurality of input regions and is configured to control vibratory magnitude settings and vibratory pattern settings of the vibratory actuators 111, 112 based upon inputs on the input regions 131. The control module 130 therefore preferably includes a button or other type of input region 131 configured to receive an input from a user, the processor 132, and the driver(s) 133 (e.g., a motor driver, as described above).

The processor 132 is preferably a microprocessor, such as the ATmega328 microcontroller by Atmel Corporation, configured to read analog pins or digital bits set by the input regions 131 and further configured to set digital output pins to control the vibratory actuators 111, 112 or haptic stimulation unit(s). The processor 132 preferably controls operation of each vibratory actuator 111, 112 or a haptic stimulation unit by modulating the state of a digital output pin connected to a motor driver 133 (e.g., a MOSFET, an H-bridge), wherein the driver 133 changes state according to the digital output pin to open and close a high-current path to the battery 121 (or power-conditioning circuit) to disable and enable the vibratory actuators 111, 112 (or haptic stimulation unit), respectively. The driver 133 therefore can function to isolate the processor 132 from high-current signals. The processor 132 preferably controls an output pin connected to the driver 133 via pulse-width modulation at a frequency less than a maximum switching frequency of the driver 133, thus enabling the processor 132 to pulse the output pin at a duty cycle between 0% and 100% to vary the magnitude of vibrations output by the vibratory actuators 111, 112 between full stop and full speed. The processor 132 preferably sets the state of each digital output pin, connected to a vibratory actuator or haptic stimulation unit via a driver, independently such that the vibratory actuators or haptic stimulation units can be independently controlled. However, the processor 132 can set the state of one digital output pin connected to one driver electrically coupled to two or more vibratory actuators or haptic stimulation units. Alternatively, the processor 132 can set the state of one digital output pin connected to two drivers, each electrically coupled to one or more vibratory actuators or haptic stimulation units. Yet alternatively, the processor 132 can communicate with a multiplexer via two or more digital output pins (e.g., one input pin and one output pin) to control three or more vibratory actuators or haptic stimulation units, via drivers, with a minimum of digital output pins. However, the processor 132 can function in any other way to control the vibratory actuators 111, 112 or haptic stimulation unit(s).

The processor 132 preferably stores vibratory patterns or other haptic stimulation patterns such that the user can cycle through the vibratory patterns to access different sensory stimulations. For example, the processor 132 can store a steady vibration pattern, ramp patterns, pulsation patterns, pseudo-random pulsation or ramp patterns, or any combinations thereof. The processor preferably stores the stimulation patterns in the ROM and then transfers the patterns internally and on the fly to the processor's RAM. The processor 132 can stored the patterns in compressed format then decompress the patterns, which can enable the processor 132 to phase shift, time stretch, time shrink, or modify the amplitude of the patterns.

The processor 132 preferably accesses a pre-loaded set of vibratory patterns or other haptic stimulation patterns. However, the control module 130 can download additional stimulation patterns, such as through a computer when the male power port 124 is connected thereto. In one example, the user can download stimulation patterns through a website or native application hosted by a vibrator or sex toy manufacture, hosted on a forum including users of similar devices, or sent to the user by a friend, partner, or sex toy-related entity. Such predefined stimulation patterns can be recommended to the user by others with similar devices, such as through a social network, a blog, a forum, or a website hosted by a sex toy-related entity. In another example, the user can create a custom stimulation pattern through a website or native application executing on a computer or mobile device, and the user can then transfer the custom pattern to the device 100 for subsequent use.

In one variation, the device 100 is configured to operate in a charging mode in the first variation, a stimulation mode in the second configuration, and a secondary function mode in either of the first and second configurations. Generally, the processor 132 preferably identifies the current configuration of the device 100 and (seamlessly) adjusts operation or current function accordingly. For example, in the secondary function mode, the device 100 can function as a wired or wireless mass storage device (MSD) or a human interface device (HID) in which battery status or diagnostic information can be communicated to the user. Furthermore, the user can access the secondary function mode to lock, password protect, change the order of patterns, or create presets on the device 100, such as from an external USB host device executing supplied software.

The input regions 131 preferably include a set of buttons that communicate with the processor 132 to set or modify operation of the device 100. Each button is preferably a mechanical momentary pushbutton coupled to a pull-down resistor and to a digital input pin of the processor 132. However, the input regions 131 can include a Hall effect switch, an optical switch, a capacitive touch sensor, a resistive touch sensor, an acoustic touch sensor, or any other suitable type of tactile switch or button. Furthermore, each input region 131 preferably provides tactile feedback to the user, such as in the form of a click, when the input region 131 is depressed or contacted by the user.

In one example implementation, the input regions 131 include a [POWER/MODE] button, a [DECREASE INTENSITY] button, and an [INCREASE INTENSITY] button. In this example implementation, the user can power the device 100 ON by depressing the [POWER/MODE] button, change a vibratory pattern setting by depressing the [POWER/MODE] button, increase the intensity of vibration (or speed of a vibratory pattern) by depressing the [INCREASE INTENSITY] button, decrease the intensity of vibration (or speed of a vibratory pattern) by depressing the [DECREASE INTENSITY] button, and power the device 100 OFF by depressing and holding the [POWER/MODE] button.

In a similar example implementation, the input regions 131 can include a [POWER/MODE] button and an [INTENSITY] button, wherein the user can power the device 100 ON by depressing the [POWER/MODE] button, cycle through vibratory pattern settings by depressing the [POWER/MODE], cycle through vibration intensity levels by depressing the [INTENSITY] button, and power the device 100 OFF by depressing both buttons simultaneously. However, the processor 132 can modify operation of the device 100 according to any other single or combination of inputs at the input regions 131.

Alternatively, the input region can include a dial, a slide, a series of toggle switches, or other type of input region, button, or control. For example, the input regions 131 can include a dial, through which the user can adjust the stimulation intensity, and a momentary mechanical pushbutton, through which the user can power the device 100 ON and OFF and cycle through available modes (e.g., vibratory pattern settings). However, the input regions 131 of the control module 130 can be of any other type, capture any other user input, and modify operation of the device 100 in any other way. Furthermore, the input regions 131 are preferably backlit, such as with an LED arranged behind a translucent button. In this implementation, the backlights preferably depict the level of charge of the battery 121 when charging in the first configuration. For example in the first configuration, the backlights can blink slowly when the battery 121 has minimal charge and blink faster as the energy content of the battery 121 increases, wherein the backlights show solid with the battery 121 is fully charged. This functionality is preferably controlled by the processor 132, and the backlights can be any other suitable light-output device or lamp arranged in any other way on the device 100.

The processor 132 is preferably further configured to enter a sleep state, such as after a threshold period of time without use and/or given a user input to turn the device 100 OFF, in order to minimize current drain from the battery 121. In this implementation, a user input at an input region 131 preferably trips an interrupt of the processor 132, which triggers the processor 132 to exit the sleep or OFF state. When powering ON, the processor 132 can pulse a vibratory actuator or haptic stimulation unit in a pattern indicative of the charge on the battery 121. For example, the processor 132 can pulse a vibratory actuator five times when the battery 121 that has between 80 and 100% charge, four times when the battery 121 that has 60 to 80% charge, three time when the battery 121 that has 40 to 60% charge, etc. Alternatively, when ON, the processor 132 can adjust the intensity of a backlight behind an input region or the intensity level of any other lamp, LED, or output mechanism on or in the device 100 to indicate battery level.

In one example implementation, the input regions 131 of the control module 130 are arranged on or in the power module 120, as shown in FIG. 1. In this implementation, the processor 132 and the drivers 133 are also arranged within the power module 120 such that the processor 132 can substantially directly access input region outputs and substantially directly communicate with the drivers 133 (e.g., not through the power ports). In this variation, high-current drive signals for the vibratory actuators 111, 112 or haptic stimulation unit are preferably communicated to the interaction module 110 through the power ports. Furthermore, in this example implementation, the input regions 131 are preferably arranged on the power module 120 opposite the male power port 124 (and opposite the interaction module 110) such that the input regions 131 are substantially accessible to the user while holding the power module 120, which preferably transmits less vibration or other haptic stimulation into a hand of the user.

In another example implementation, the input regions 131 of the control module 130 and the processor 132 are also arranged on or in the power module 120, and the drivers 133 are arranged within the interaction module 110. In this example implementation, the processor 132 preferably communicates with the drivers 133 over the power ports, as described above. Furthermore, in this example implementation, the input regions 131 are preferably arranged on the power module 120 opposite the male power port 124 (and opposite the interaction module 110) such that the input regions 131 are substantially accessible to the user while holding the power module 120, as described above.

In yet another example implementation, the input regions 131 are arranged on or in the interaction module 110. In this example implementation, the processor 132 is also preferably arranged within the interaction module 110 and is powered by the battery 121 through the power ports. The processor 132 can therefore also communicate substantially directly with the drivers 133 to control the vibration actuators 111, 112 or the haptic stimulation unit(s). Alternatively, the processor 132 can be arranged within the power module 120 and access input region states through the power module 120, such as by communicating, via one-wire or I2C communication protocol, with a parallel-in, serial-out (PISO) shift register electrically coupled to the input regions 131. However, the input regions 131, processor 132, and drivers 133 can be arranged in any other way within the device 100 and communicate with one another over any other suitable connection or protocol.

One variation of the device 100 further includes a memory module. The memory module is preferably a solid state read/write hard drive or flash memory configured to store digital data for future access and/or erasure. The memory module is preferably arranged within the power module 120 such that the male power port 124 can communicate data digitally between the memory module and a connected external electronic device in the first configuration. In the implementation described above in which the male power port 124 is a male USB plug including a ground pin, a power pin, and two digital output pins, the memory module preferably downloads data via the ground pin and a digital input pin and preferably uploads data via the ground pin and a digital output pin. Therefore, in the first configuration, the power module 120 can additionally function as a flash drive or memory stick. Furthermore, the processor 132 can access data stored on the memory module, such as vibratory patterns or user vibratory preferences, to control device settings when in use (i.e. in the second configuration). However, the memory module can be arranged in any other way within the device 100 and can communicate with any other component internal or external the device 100.

The memory module is preferably configured to store personal content of the user. Data stored on the memory module is preferably selected by the user and pushed to the device 100 in the first configuration. Additionally or alternatively, the memory module can receive data or personal content wirelessly, such as from a smartphone or tablet via a wireless communication module incorporated into the device 100. For example, the wireless communication module can access a smartphone, via a Wi-Fi connection, to download personal video and images of the user engaging in sexual intercourse and other sexual acts, wherein the video and images are stored on the memory module. The wireless communication and memory modules can access and store such data in real time (i.e. while personal content is generated) and/or after the fact, such as when the user subsequently couples the device 100, either wireless or physically, to an external electronic device. Similarly, the memory module can wirelessly broadcast personal content to an external electronic device. For example, the user can manipulate one or more input regions 131 to broadcast a video or image from the memory module to an external electronic device (e.g., a television, gaming console or receiver coupled to a television, a smartphone, a tablet), and the user can further manipulate one or more input regions 131 to play, pause, fast forward, rewind, and/or thumb through the video or image. Furthermore, the memory module can be locked or password protected to secure stored data from unwanted or unwarranted access. Therefore, in this variation, the device 100 can function not only as a sex toy by also as a repository for personal and/or sex-related content such that physical and digital sexual paraphernalia can be embodied (e.g., accessed) in a single device.

In a similar variation, the device 100 can further include an auditory element that outputs an audio signal. The auditory element is preferably a speaker arranged within the power module 120, and the auditory element preferably plays music, male or female sex noises, or other sounds to augment the user's sexual experience. Auditory or sound data is preferably stored on the memory module and access by the processor 132, which controls the auditory element through a speaker driver. However, the auditory element can be arranged in any other way within the device 100, can be controlled in any other way, and can output any other auditory signal.

In one variation of the device 100, the power module 120 further includes a secondary vibratory actuator or haptic stimulation unit. The secondary vibratory actuator or haptic stimulation unit is also preferably powered by the battery 121, through a driver, and is also preferably controlled by the processor 132. In one example implementation, the interaction module 110 includes a vibratory actuator 111 within an elongated member suitable for inter-vaginal stimulation, and the power module 120 includes a secondary vibratory actuator within a short curved member suitable for clitoral stimulation, wherein the power and interaction modules 1110, 120 assemble in the second configuration to simultaneously stimulate both the G-spot and the clitoris of a female user. Alternatively, the power module 120 can include a heating element and can mechanically couple to the interaction module 110 that includes a vibratory actuator. However, the power module 120 can include any other suitable secondary vibratory actuator or haptic stimulation unit in any other quantity to cooperate with the interaction module 110 to sexually stimulate the user.

As shown in FIG. 8, the power module 120 can be further configured to mechanically couple to interaction modules of various shapes, geometries, and configurations. The power module 120 can therefore separately power (and control) multiple interaction modules such that the user can customize the device 100 for a particular sexual experience or for a particular sexual stimulation, use, or need. In an example implementation, the device 100 can define a sexual stimulation kit with interchangeable interaction modules, including a clitoral stimulation module 110, an inter-vaginal stimulation module 110b, a rectal-stimulation module 110c, and a combination vaginal- and clitoral-stimulation module 110d, such that the user can assemble the power module 120 with different interaction modules suitable for stimulation of different sex organs. In this variation, the processor 132 and drivers 133 are preferably arranged within the power module 120 to reduce part count across the sexual stimulation kit. Each interaction module can be associated with different stimulation patterns, settings, or user preferences, and the processor 132 in the power module 120 therefore preferably identifies each unique type of interaction module such that each interaction module can be properly controlled. In one example implementation, the processor 132 reads a resistor value coupled to a pin of the female power port of an interaction module when the power and interaction modules are assembled, wherein each type of interaction module includes a resistor of a value unique amongst the set (or kit) of interaction modules. In this example implementation, the resistor can be a component in a voltage divider defined in part by the interaction module 110 and/or the power module 120, wherein an analog input pin of the processor 132 is coupled to an output of the voltage divider, and wherein the processor 132 implements an analog-to-digital converter to read the output of the voltage divider and identify the type of connected interaction module 110. In another example implementation, the processor 132 in the power module 120 receives, via the power ports, a serial code from a secondary processor, timer, or other circuit within each interaction module when connected thereto, wherein the serial code is unique to each type of interaction module. However, the processor 132 in the power module 120 can identify the type of a connected interaction module in any other way or through any other hardware or software component. Furthermore and as described above, the processor 132 can substantially seamlessly modify operation or current function of the device 100 according to a current configuration, attachment, mode, input, etc.

2. Vibratory Actuator

As shown in FIG. 5, the vibratory actuator 200 for a sexual stimulation device includes: a motor including an output shaft 215; a counterweight 220 coupled to the output shaft 215; a enclosure 230 enclosing the counterweight 220 and the output shaft 215; a first isolator 240 coupled to the motor 210 opposite the output shaft 215 and configured to pivotably couple the motor 210 to a motor support structure 213; and a second isolator 250 coupled to the motor 210 adjacent the first isolator 240 and configured to contact a surface of the motor support structure 213 to define a pivot endstop.

The vibratory actuator 200 preferably outputs vibrations proximal a free end but limits transmission of vibrations into the support structure 213 (e.g., the housing 113 of the interaction module 110 described above) that captures an opposite end of the vibratory actuator 200 via the isolators 240, 250. The vibratory actuator 200 is preferably suitable as a haptic stimulation unit within a sexual stimulation device, such as the device 100 disclosed above. Because the vibratory actuator 200 substantially minimizes vibratory transmission into the support structure 213, in comparison with a device with a substantially rigid motor mount, a device incorporating the vibratory actuator 200 can be more comfortable for a user holding the device, can be substantially quieter without sacrificing vibratory output or magnitude, and can be substantially more efficient by focusing vibration to a particular region of the device configured to stimulate a sex organ.

As shown in FIG. 5, the motor 210 includes an output shaft 215, and the output shaft 215 preferably extends from a single face of the motor 210. As described above, the motor 210 is preferably a DC micromotor, though the motor 210 can alternatively be a stepper motor, a servomotor, or a brushless motor of any other suitable size. The motor 210 preferably includes a motor casing 217 that is circular in cross-section, though the motor 210 or motor casing 217 can be of any other suitable geometry.

The counterweight 220 is coupled to the output shaft 215 and preferably induces a vibration when rotated by the motor 210. The counterweight 220 is preferably pressed onto an end of the output shaft 215, but can alternatively be bonded, fastened, pinched, brazed, or otherwise mechanically coupled to the output shaft 215. The counterweight 220 is preferably sized for the motor size, motor speed, and desired vibration frequency and/or magnitude. The counterweight 220 is preferably a substantially dense material, such as iron or brass, though the counterweight 220 can be any other suitable material.

As described above, the enclosure 230 encloses the counterweight 220 and the output shaft 215. The enclosure 230 is preferably a spun, drawn, stamped, or machined metal enclosure 230 that slides over the output-side of the motor 210 to shield the output shaft 215 and the counterweight 220. For example, the enclosure 230 can be stainless steel, cold-rolled steel with a zinc plating, aluminum, or brass. However, the enclosure 230 can be any other suitable material, such as plastic (e.g., HDPE, nylon), and can be manufactured via any other suitable technique, such as injection molding. As shown in FIG. 6 and described above, the enclosure 230 preferably includes an internal shoulder that engages the face of the motor 210 at the output side to locate the motor 210 longitudinally within the enclosure 230. The internal profile of the enclosure 230 preferably accommodates the motor 210 via a slip fit with minimal spacing (e.g., <0.001" or 0.025 mm) between the internal wall of the enclosure 230 and the exterior surface of the motor casing 217, though the motor 210 can be installed in the enclosure 230 with any other suitable fit.

The first isolator 240 is coupled to the motor 210 opposite the output shaft 215 and is configured to pivotably couple the motor 210 to the motor support structure 213. The second isolator 250 is coupled to the motor 210 adjacent the first isolator 240 and is configured to contact a surface of the motor support structure 213 to define the pivot endstop. As described above and shown in FIG. 6, the first and second isolators preferably cooperate to pivotably couple the motor 210 to the motor support structure 213, to isolate the support structure 213 from vibrations induced by the vibratory actuator 200, and to limit maximum off-axis deflection of the vibratory actuator 200 relative to the support structure 213. However, the isolators can alternatively constrain the vibratory actuator 200 in any other way, such as by limiting off-axis deflection of the vibratory actuator 200 within a single plane or by permitting the vibratory actuator 200 to translate axially or cross-axially proximal the first or second isolators and relative to the support structure 213.

The first isolator 240 is preferably an o-ring of a first outer diameter and a first cross-sectional area, and the second isolator 250 is preferably an o-ring of a second outer diameter less than the first outer diameter and a second cross-sectional area less than the first cross-sectional area. As described above, the first and second isolators are preferably silicone o-rings of circular cross-section, such a Viton or buna o-rings. However, the isolators 240, 250 can be of any other material, form, or geometry.

As shown in FIGS. 5 and 6, the vibratory actuator 200 preferably further includes a plug 270 pressed into the open end of the enclosure 230 to constrain the motor 210. The plug 270 preferably includes a first circular recess or groove configured to receive the first isolator 240, wherein the first isolator 240 can further engage a recess or groove in the support structure 213 to couple the vibratory actuator 200 to the support structure 213. The plug 270 preferably also includes a second circular recess proximal the first circular recess and configured to receive the second isolator 250 such that the second isolator 250 can define a compressible (or 'soft') endstop against a surface of the support structure 213 as the vibratory actuator 200 pivots about the first isolator 240, as shown in FIG. 6. The plug 270 preferably further includes a through bore such that motor leads 260 can pass through the bore and electrically couple to a PCB, motor driver, or other suitable electrical component, as described above. The plug 270 is preferably a machined aluminum plug 270 but can be any other suitable material and manufactured in any other way. Furthermore, features of the plug 270, such as the circular recesses or grooves, can be incorporated into the motor casing 217 and/or into the enclosure 230 to enable similar functionality in variations of the vibratory actuator 200 that exclude the plug 270. However, the vibratory actuator 200 can include any other component that functions in any other way or cooperates with any other component of the vibratory actuator 200 to output vibrations suitable to for a sexual stimulation device, such as the device 100 described above.

As a person skilled in the art will recognize from the previous detailed description and from the figures and claims, modifications and changes can be made to the preferred embodiments of the invention without departing from the scope of this invention as defined in the following claims.

We claim:

1. A device for sexual stimulation, comprising:
   an interaction module comprising
      a first port comprising a power pin and a first ground pin and
      a haptic stimulation unit electrically coupled to the power pin and to the first ground pin; and
   a control module comprising
      a second port comprising an input pin, an output pin, and a second ground pin, configured to transiently engage a standardized powered data port of an external device in a first configuration, and configured to transiently engage the first port in a second configuration,
      a rechargeable battery,
      a charging circuit electrically coupled to the second port and configured to control current sourced from an external device over the input pin and the second ground pin to charge the rechargeable battery in the first configuration,
      an input region, and
      an actuator driver configured to control power transmission from the rechargeable battery to the haptic stimulation unit, in the second configuration, via the output pin and the second ground pin, wherein the output pin is electrically coupled to the power pin and the second ground pin is electrically coupled to the first ground pin in response to an input on the input region wherein the actuator driver comprises at least one power transistor and a processor, the at least one power transistor electrically coupled to the rechargeable battery, to the output pin, and to the second ground pin, the processor configured to set a current vibratory pattern setting in response to an input on the input region and to control the at least one power transistor according to the current vibratory pattern setting.

2. The device of claim 1, wherein the input region comprises a mode region, a first intensity region, and a second intensity region, wherein the processor is configured to cycle through a set of stored vibratory pattern settings in response to an input on the mode region, to increase an intensity of the current vibratory pattern setting in response to an input on the first intensity region, and to decrease an intensity of the current vibratory pattern setting in response to an input on the second intensity region.

3. The device of claim 1, wherein the interaction module defines an elongated member extending along an axis parallel to a direction of insertion of the second port into the first port.

4. The device of claim 1, wherein the haptic stimulation unit comprises a vibratory actuator comprising a direct-current electrical rotary motor and an eccentric mass coupled to an output shaft of the motor.

5. The device of claim 4, wherein the interaction module further comprises a support structure, and wherein the vibratory actuator comprises a housing enclosing the eccentric mass and the output shaft, a first isolator coupled to the motor opposite the eccentric mass and configured to pivotably couple the motor to the support structure, and a second isolator coupled to the motor adjacent the first isolator and configured to contact a surface of the support structure to define a pivot endstop for the vibratory actuator.

6. The device of claim 5, wherein the first isolator and the second isolator are configured to damp transmission of vibrations, generated by the vibratory actuator, into the support structure.

7. The device of claim 1, wherein the first port further comprises a second power pin, wherein the interaction module further comprises a second haptic stimulation unit electrically coupled to the second power pin and to the first ground pin, wherein the second port further comprises a second output pin, and wherein the actuator driver is further configured to control power transmission from the rechargeable battery to the second haptic stimulation unit, in the second configuration, via the second output pin, wherein the second output pin is electrically coupled to the second power pin, and the second ground pin electrically coupled to the first ground pin in response to an input on the input region.

8. The device of claim 7, wherein the haptic stimulation unit comprises a first vibratory actuator and the second haptic stimulation unit comprises a second vibratory actuator, the first vibratory actuator and the second vibratory actuator adjacent and substantially parallel.

9. The device of claim 7, wherein the actuator driver comprises a first power transistor and a second power transistor, wherein the first power transistor is electrically coupled to the rechargeable battery, to the output pin, and to the second ground pin, the second power transistor electrically coupled to the rechargeable battery, to the second output pin, and to the second ground pin, the processor configured to control the first power transistor and to control the second power transistor independently according to an input on the input region.

10. The device of claim 1, wherein the first port comprises a female universal serial bus receptacle, and wherein the second port comprises a male universal serial bus plug.

11. The device of claim 1, wherein the actuator driver is configured to communicate a pulse-width modulated power signal from the rechargeable battery to the haptic stimulation unit over the output pin electrically coupled to the power pin and the second ground pin electrically coupled to the first ground pin in the second configuration.

12. The device of claim 1, wherein the control module further comprises a memory module, wherein the second port is configured to communicate data serially between the memory module and an external computing device over the output pin, a second output pin, and the second ground pin.

13. The device of claim 1, wherein the charging circuit is configured to communicate a power request signal to a computing device over the output pin in the first configuration.

14. A device for sexual stimulation, comprising:
an interaction module comprising
a first port comprising a first power pin, a first ground pin, and a first data pin,
a haptic stimulation unit electrically coupled to the first ground pin, and
an actuator driver configured to selectively electrically couple the haptic stimulation unit to the first power pin according to a digital control signal received over the first data pin; and
a control module comprising
a second port comprising a second power pin, a second data pin, and a second ground pin, configured to transiently engage a standardized powered data port of a computing device in a first configuration, and configured to transiently engage the first port in a second configuration,
a rechargeable battery,
a charging circuit electrically coupled to the second port and configured to control current sourced from a computing device over the second power pin and the second ground pin to charge the rechargeable battery in the first configuration,
a memory module configured to communicate data serially with a computing device over the second data pin and the second ground pin in the first configuration,
an input region, and
a processor configured to communicate a digital control signal to the actuator driver over the second data pin, wherein the second data pin is electrically coupled to the first data pin in the second configuration in response to an input on the input region.

15. The device of claim 14, wherein the first port further comprises a third data pin, wherein the interaction module further comprises a second haptic stimulation unit electrically coupled to the first ground pin and a second actuator driver configured to selectively electrically couple the second haptic stimulation unit to the first power pin according to a second digital control signal received over the second data pin, wherein the second port further comprises a fourth data pin, and wherein the processor is further configured to communicate a second digital control signal to the second actuator driver over the fourth data pin, wherein the fourth data pin is electrically coupled to the third data pin in the second configuration, the second digital control signal independent of the digital control signal.

* * * * *